(12) United States Patent
Segal

(10) Patent No.: US 9,694,197 B2
(45) Date of Patent: Jul. 4, 2017

(54) METHOD AND DEVICE FOR ENHANCING BRAIN ACTIVITY

(75) Inventor: Yaron Segal, Jerusalem (IL)

(73) Assignee: BrainQ Technologies Ltd., Jerusalem (IL)

( * ) Notice: Subject to any disclaimer, the term of this patent is extended or adjusted under 35 U.S.C. 154(b) by 428 days.

(21) Appl. No.: 14/344,606

(22) PCT Filed: Jun. 21, 2012

(86) PCT No.: PCT/IL2012/000255
§ 371 (c)(1),
(2), (4) Date: Oct. 5, 2014

(87) PCT Pub. No.: WO2013/038400
PCT Pub. Date: Mar. 21, 2013

(65) Prior Publication Data
US 2015/0018706 A1  Jan. 15, 2015

Related U.S. Application Data

(60) Provisional application No. 61/533,917, filed on Sep. 13, 2011.

(51) Int. Cl.
*A61N 2/04* (2006.01)
*A61N 2/02* (2006.01)
(Continued)

(52) U.S. Cl.
CPC .............. *A61N 2/02* (2013.01); *A61B 5/0476* (2013.01); *A61B 5/05* (2013.01); *A61B 5/055* (2013.01); *A61B 5/4064* (2013.01); *A61N 2/006* (2013.01)

(58) Field of Classification Search
CPC .............................................. A61N 2/00–2/12
See application file for complete search history.

(56) References Cited

U.S. PATENT DOCUMENTS

| 2004/0002635 A1 | 1/2004 | Hargrove et al. |
| 2010/0016651 A1* | 1/2010 | Sivo ......................... A61N 1/40 600/14 |

(Continued)

OTHER PUBLICATIONS

Gregory Emery et al. "Asymmetric Rab11 Endosomes Regulate Delta Recycling and Specify Cell Fate in the Drosophila Nervous System" Cell, vol. 122, 763-773, Sep. 9, 2005.

(Continued)

*Primary Examiner* — Charles A Marmor, II
*Assistant Examiner* — Thaddeus Cox
(74) *Attorney, Agent, or Firm* — Pearl Cohen Zedek Latzer Baratz LLP

(57) ABSTRACT

An apparatus is provided for stimulating brain neural networks of a subject comprising: at least one transmitter configured to generate an electromagnetic field through the brain neural networks of a subject, at least one brain wave measuring device for detecting subject brain wave frequency, a CPU for processing data concerned with detection of brain wave frequency of a subject, having a database for storing and analyzing natural and affected brain scans, and at least one computer readable medium containing a predetermined protocol for transmission of the electromagnetic wave frequency profiles. The apparatus further provides a resonance effect thereby inducing newly generated brain cells to migrate toward a brain tissue area having the pathology or lesion of interest, and initiating new brain pathways at the brain region of interest.

15 Claims, 23 Drawing Sheets

Figure 1A:
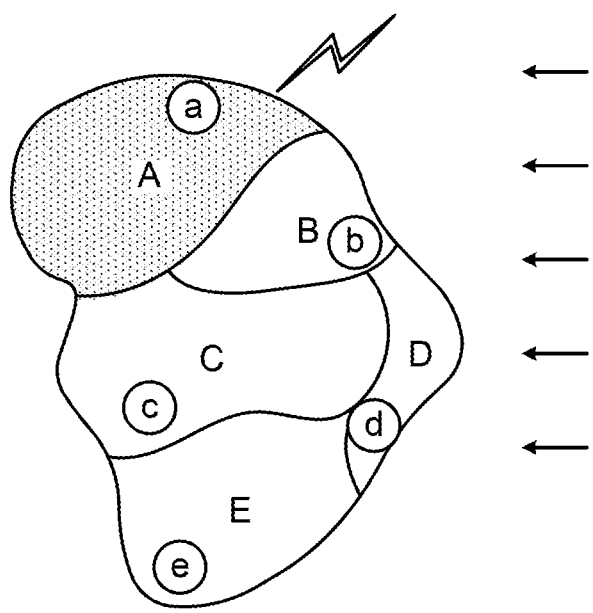

(51) Int. Cl.
*A61B 5/0476* (2006.01)
*A61B 5/05* (2006.01)
*A61B 5/00* (2006.01)
*A61N 2/00* (2006.01)
*A61B 5/055* (2006.01)

(56) References Cited

U.S. PATENT DOCUMENTS

| | | |
|---|---|---|
| 2010/0210894 A1 | 8/2010 | Pascual-Leone et al. |
| 2011/0046432 A1 | 2/2011 | Simon et al. |
| 2011/0112427 A1 | 5/2011 | Phillips et al. |
| 2011/0190849 A1 | 8/2011 | Faltys et al. |

OTHER PUBLICATIONS

Ye Xiong et al. "Neurorestorative Treatments for Traumatic Brain Injury" Discov Med. Nov. 2010 ; 10(54): 434-442.

R. Shayna Rosenbaum et al. "The case of K.C.: contributions of a memory-impaired person to memory theory" Neuropsychologia 43 (2005) 989-1021.

L. Niehaus et al. "Abnormal postexcitatory and interhemispheric motor cortex inhibition in writer's cramp" Feb. 2001, vol. 248, Issue 1, pp. 51-52.

Michael J. Kahana "The Cognitive Correlates of Human Brain Oscillations" The Journal of Neuroscience, Feb. 8, 2006, 26(6):1669-1672.

Steven G. Kernie "Brain Remodeling Due to Neuronal and Astrocytic Proliferation After Controlled Cortical Injury in Mice" Journal of Neuroscience Research 66:317-326, Oct. 25, 2011.

International Search Report for Application No. PCT/IL2012/000255, mailed on Oct. 22, 2012.

European Search Report of European Application No. EP 12 83 1890 mailed Mar. 17, 2015.

\* cited by examiner

METHOD AND DEVICE FOR ENHANCING BRAIN ACTIVITY

CROSS-REFERENCE TO RELATED APPLICATIONS

This application is a National Phase Application of PCT International Application No. PCT/IL2012/000255, International Filing Date Jun. 21, 2012, claiming priority of U.S. Patent Application No. 61/533,917, filed Sep. 13, 2011, which is hereby incorporated by reference.

FIELD OF THE INNOVATION

This invention relates to electromagnetic devices and methods for therapeutically treating body tissue, and more particularly to a device for and a method of enhancing and stimulating nervous systems activity and related molecular events using a variety of electromagnetic energy frequencies.

BACKGROUND

The ability of the brain to change in response to experience and use is well recognized as brain plasticity, and is a fundamental property of the brain nervous system. This adaptive behavior of the brain allows it to learn and remember, to refine movements and to recover function after injury.

Many forms of brain's cellular plasticity based on new sensitive research methods are known in the art. In some distinct areas of all adult mammalian brains (the subventricular zone, SVZ, of the lateral ventricle and the dentate gyrus subgranular zone, SGZ, of the hippocampus) new neurons and glia cells originating from neural stem cells are continuously produced. In a normal adult brain, SVZ-derived neuroblasts migrate along the rostral migratory stream to the olfactory bulb, where these cells differentiate into interneurons to replace those that have died.

Rats that have experienced traumatic brain injury (TBI) display cognitive recovery as early as 2 weeks after injury (Emery et al., 2005). At the same time, newborn neurons extend axonal projections into the hippocampal CA3 region, a phenomenon which possibly contributes to the observed recovery. Following TBI, neuroblasts migrating from the SVZ can differentiate into neurons and glia (Kernie et al., 2001). A recent review by Xiong et al. (Discov Med 2010) discusses selected cell-based and pharmacological therapies, that activate and amplify these endogenous restorative brain plasticity processes to promote both repair and regeneration of an injured brain tissue and that improve functional recovery after TBI.

It is also noted that learning co exists with higher brain activity (Rosenbaum et al 2005), thus suggesting that if a proper training is employed, the brain plasticity will allow the regions subjected to the training to improve their activity in terms of both higher connectivity between existing brain cells and the number of cells functioning in the affected brain systems.

Niehaus (et al. 2001) reported that stimulation of the brain in 10 hz frequency has an effect on the autonomic nervous system. It is shown to be possible to stimulate the sympathetic nervous system by artificial electromagnetic transmissions operating at 10 Hz, with no significant interference with other nerve pathways. Kahana (2006) showed that brain activity can be traced using EEG (Electroencephalography).

During the development stages of the human brain, certain proteins direct newly generated brain cells in the appropriate time through brain's buildup into specific nervous systems, in which they "learn" to perform and to handle the developing body.

This process is controlled by the amount of protein synthesized at the given stage, which is governed by the genetic heritage of an individual.

It therefore remains a long felt and unmet need to provide novel means and methods of treatment which are personalized to individual patients.

SUMMARY OF THE INVENTION

It is one object of the invention to provide an apparatus for stimulating brain neural networks of a subject comprising: (a) at least one transmitter configured to generate an electromagnetic field through the brain neural networks of a subject, (b) at least one brain wave measuring device for detecting subject brain wave frequency, (c) a first CPU for processing data concerned with detection of brain wave frequency of a subject, comprising a database for storing and analyzing natural and affected brain scans, (d) a second CPU for processing data concerned with transmission of wave frequency to a specific brain tissue having an activity of interest, and (e) at least one computer readable medium containing a predetermined protocol for transmission of the electromagnetic wave frequency profiles by the transmitter. The computer readable medium is adapted to instruct the transmitter to provide a resonance effect thereby inducing newly generated brain cells to migrate toward a brain tissue area having the pathology or lesion of interest, and initiating new brain pathways at the brain region of interest.

It is another object of the invention to disclose the detailed above apparatus, further comprising a positioning system configured to maintain the subject head in a predetermined position respective to the transmitter.

It is another object of the invention to disclose the detailed above apparatus, wherein the transmitter is adapted for providing the electromagnetic field useful stimulating the targeted brain system by means of inducing a resonance effect between the frequency of the magnetic field and the natural brain wave frequency of the subject brain system.

It is another object of the invention to disclose the detailed above apparatus, wherein the resonance effect is defined by the enhanced activity visible as a consequence of brain mapping.

It is another object of the invention to disclose the detailed above apparatus, wherein the resonance effect generates an electro-chemical transmission in the nerve cells and neuron of the determined nervous system.

It is another object of the invention to disclose the detailed above apparatus, wherein the CPU further includes a database comprising data useful for mapping the brain wave of a subject in order to adjust to the protocol of the subject.

It is another object of the invention to disclose the detailed above apparatus, wherein the CPU is further adapted to control the wave generator and the treatment timing.

It is another object of the invention to disclose the detailed above apparatus, wherein the predetermined protocol includes a plurality of distinct frequencies within the range of the distinct brain activities.

It is another object of the invention to disclose the detailed above apparatus, wherein the transmitter comprises a coil; the coil is a Helmholtz coil, having a turn diameter greater than an average sized human's skull.

It is another object of the invention to disclose the apparatus detailed above, wherein a subject's head may be placed inside the coil without specifically locating it since the coil has a uniform field inside and the neurons in the brain do not have a preferred alignment.

It is another object of the invention to disclose the detailed above apparatus, wherein the frequencies are conformed in accordance to specific brain tissue known to be capable of having an activity of interest.

It is another object of the invention to disclose the detailed above apparatus, wherein the magnetic field is transmitted in a selected frequency for at least one session.

It is another object of the invention to disclose the detailed above apparatus, wherein the transmission of the magnetic field is synchronized with the cell cycle for migrating nascent brain cells.

It is another object of the invention to disclose the detailed above apparatus, further wherein the stimulating procedure results the creation of the new brain paths of interest.

It is another object of the invention to disclose the detailed above apparatus, further wherein the transmitter operates within the frequency range of about 0.01 Hz to 100 Hz.

It is another object of the invention to disclose the detailed above apparatus, wherein the electromagnetic field is administered in a range between about 10 in the power of −6 Gauss to 100 gauss that affect the desired nervous system.

It is another object of the invention to disclose the detailed above apparatus, is applied to certain diseases and syndromes such as Autism, Famillial dysautonomia, Brather Willy, Epilepsy, the spectrum of PDD, the spectrum of HDAD, retardation, CP and other brain related syndromes.

It is another object of the invention to disclose the detailed above apparatus, further wherein the apparatus decrease the symptoms of brain injuries (trauma), stroke, multiple sclerosis (MS), symptoms of Alzheimer, dementia, Parkinson and any other degradation diseases of the brain.

It is another object of the invention to disclose the detailed above apparatus, wherein the treatment protocol is adapted for determining frequency, level and duration of the current supplied to the transmitter according to a subject brain system, specified to be stimulated.

It is another object of the invention to disclose the detailed above apparatus, wherein the brain waves measuring device is selected from a group consisting of: EEG, MEG or by any other acceptable monitoring means.

It is another object of the invention to disclose the detailed above apparatus, wherein the brain waves measuring device comprises a combination of a sensing system such as EEG, MEG or MRI for defining the characteristics of brain waves of the predetermined brain system specified to be stimulated.

It is another object of the invention to disclose the detailed above apparatus, further wherein the measuring system is used for evaluating the results of the transmission sessions.

It is another object of the invention to disclose the detailed above apparatus, wherein the apparatus is applied to certain diseases and syndromes such as Autism, Famillial dysautonomia, Brather Willy, Epilepsy, the spectrum of PDD, the spectrum of HDAD, retardation, CP and other brain related syndromes.

It is another object of the invention to disclose the detailed above apparatus, further wherein the apparatus decrease the symptoms of brain injuries (trauma), stroke, multiple sclerosis (MS), symptoms of Alzheimer, dementia, Parkinson and any other degradation diseases of the brain.

It is a further object of the invention to provide a method for stimulating the brain neural networks of a subject comprising the steps of: (a) selecting a neural brain region of a subject, (b) providing an apparatus for stimulating the brain neural networks of a subject comprising: (i) at least one transmitter configured to generate an electromagnetic field through the nervous system of a subject; (ii) at least one brain waves measuring device for detecting subject brain wave frequency; (iii) a first CPU for processing data concerned with detection of brain wave frequency of a subject;
  (iv) a second CPU for processing data concerned with transmission of wave frequency to a specific brain tissue having an activity of interest; and (v) at least one computer readable medium containing a predetermined protocol for transmission of the electromagnetic wave frequency profiles by the transmitter;
  (c) identifying and analyzing anomalous gaps in the brainwaves of a subject;
  (d) defining a protocol, and (e) transmitting to the subject nervous system the protocol on the selected neural brain region. The step of defining the protocol includes providing an electromagnetic frequency profile including compensatory brainwaves; further wherein the protocol provides a resonance effect, thereby inducing newly generated brain cells to migrate toward a brain tissue area having the pathology or lesion of interest, and initiating new brain pathways at the neural brain region.

It is another object of the invention to disclose the method detailed above, further comprising the step of identifying a site of the pathological condition in the body of the subject, and wherein the step of selecting the body region comprises selecting a neural sensitive region of the body remote from the site.

It is another object of the invention to disclose the method detailed above, further comprising the step of transmitting variety of electromagnetic fields of specified frequencies in a homogeneous field covering the whole volume of the brain which is resonated with the specified nervous system, It is another object of the invention to disclose the method detailed above, wherein the electromagnetic field frequencies varies from about 0.01 Hz (DC) to 100 Hz, in intensities ranges from 10 in the power of −6 Gauss to 100 Gauss of transmitting duration ranges from minutes to hours.

It is another object of the invention to disclose the method detailed above, wherein the step of transmitting the neural sensitive body region with at least one wave frequency comprises transmitting the neural sensitive body region with a plurality of frequencies, and comprising the additional step of maintaining a minimum chronological spacing between successive ones of the frequencies of several minutes.

It is another object of the invention to disclose the method detailed above, wherein the resonance effect is defined by the enhanced activity visible as a consequence of brain mapping.

It is another object of the invention to disclose the method detailed above, wherein the resonance effect generates an electro-chemical transmission in the nerve cells and neuron of the determined nervous system.

It is another object of the invention to disclose the method detailed above, further comprising a positioning system configured to maintain the subject head in a predetermined position respective to the transmitter.

It is another object of the invention to disclose the method detailed above, wherein the electromagnetic field is adapted for stimulating the desired brain system by means of resonance effect between the frequency of the magnetic field and the natural brain wave frequency of the subject brain system.

It is another object of the invention to disclose the method detailed above, wherein the CPU includes a database for mapping the brain wave of a subject in order to adjust to the subject the protocol.

It is another object of the invention to disclose the method detailed above, wherein the CPU is further adapted to control the wave generator and the treatment timing.

It is another object of the invention to disclose the method detailed above, wherein the protocol includes a plurality of distinct frequencies within the range of the distinct brain activities.

It is another object of the invention to disclose the method detailed above, wherein the transmitter comprises a coil; the coil is a Helmholtz coil, having a turn diameter greater than an average sized human's skull.

It is another object of the invention to disclose the method detailed above, wherein the apparatus comprises a coil providing a uniform field to the head of the subject while the head is oriented in any convenient alignment.

It is another object of the invention to disclose the method detailed above, wherein the frequencies are conformed in accordance to specific brain tissue known to be capable of having an activity of interest.

It is another object of the invention to disclose the method detailed above, wherein the magnetic field is transmitted in a selected frequency for at least one session.

It is another object of the invention to disclose the method detailed above, wherein the transmission of the magnetic field is synchronized with the cell cycle for migrating newly generated brain cells.

It is another object of the invention to disclose the method detailed above, further wherein the stimulating procedure results the creation of the new brain paths of interest.

It is another object of the invention to disclose the method detailed above, further wherein the transmitter operates within the frequency range of about 0.01 Hz to 100 Hz.

It is another object of the invention to disclose the method detailed above, wherein the electromagnetic field is administered in a range between about 10 in the power of −6 to 100 gauss that affect the desired nervous system.

It is another object of the invention to disclose the method detailed above, is applied to certain diseases and syndromes such as Autism, Famillial dysautonomia, Brather Willy, Epilepsy, the spectrum of PDD, the spectrum of HDAD, retardation, CP and other brain related syndromes or diseases.

It is another object of the invention to disclose the method detailed above, further wherein the apparatus decrease the symptoms of brain injuries (trauma), stroke, multiple sclerosis (MS), symptoms of Alzheimer, dementia, Parkinson and any other degradation diseases of the brain.

It is another object of the invention to disclose the method detailed above, wherein the treatment protocol is adapted for determining frequency, level and duration of the current supplied to the transmitter according to a subject brain system, specified to be stimulated.

It is another object of the invention to disclose the method detailed above, wherein the brain waves measuring device is selected from a group consisting of: EEG, MEG or by any other acceptable monitoring means.

It is another object of the invention to disclose the method detailed above, wherein the brain waves measuring device comprises a combination of a sensing system such as EEG, MEG or MRI for defining the characteristics of brain waves of the predetermined brain system specified to be stimulated.

It is another object of the invention to disclose the method detailed above, further wherein the measuring system is used for evaluating the results of the transmission sessions.

It is another object of the invention to disclose the method detailed above, wherein the apparatus is applied to certain diseases and syndromes such as Autism, Famillial dysautonomia, Brather Willy, Epilepsy, the spectrum of PDD, the spectrum of HDAD, retardation, CP and other brain related syndromes.

It is another object of the invention to disclose the method detailed above, further wherein the apparatus decrease the symptoms of brain injuries (trauma), stroke, multiple sclerosis (MS), symptoms of Alzheimer, dementia, Parkinson and any other degradation diseases of the brain.

It is a further object of the invention to provide an apparatus for stimulating brain neural networks of a subject, the apparatus is adapted for transmitting electromagnetic to a region having an activity of interest A, which includes and surrounds region a having operating frequency means, $Haz_1$. The electromagnetic waves having a predetermined frequency $Haz_1$ selected as appropriate for the particular deficit region, recruit cells from region A, which respond to the same predetermined frequency as region b and induce migration of region A cells into region a. Further wherein the nervous regions such as B, C, D, E having different operating frequencies such as $Haz_2$, $Haz_3$ and $Haz_4$ will not resonate and therefore will not be active in response to the transmission.

It is a further object of the invention to provide n apparatus for stimulating brain neural networks of a subject, the apparatus is adapted for transmitting electromagnetic wave frequency to a region having an activity of interest B, which includes and surrounds region b which having operating frequency means, $Haz_2$. The electromagnetic waves having a predetermined frequency $Haz_2$ selected as appropriate for the particular deficit region, recruit cells from region B, which respond to the same predetermined frequency as region b and induce migration of region B cells into region b. Further wherein the nervous regions such as A, C, D, E having different operating frequencies such as $Haz_1$, $Haz_3$ and $Haz_4$ will not resonate and therefore will not be active in response to the transmission.

BRIEF DESCRIPTION

Figure 1B:
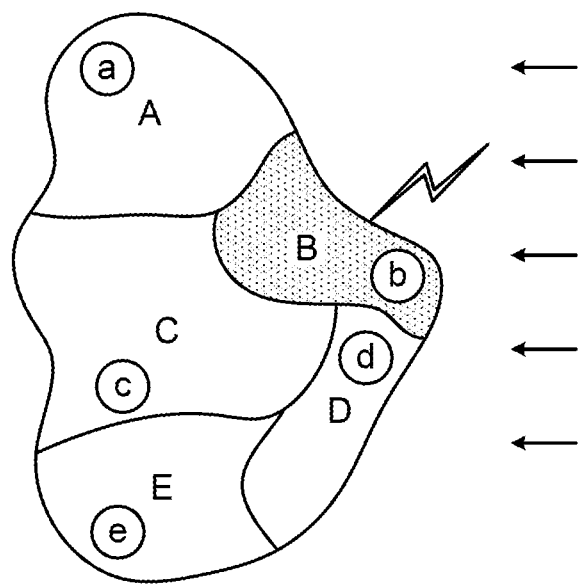
Figure 2:
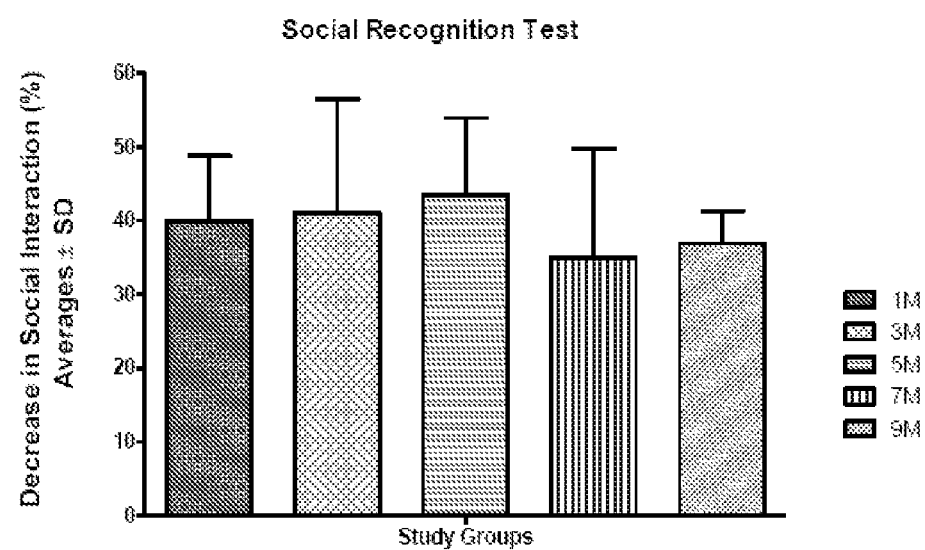
Figure 3:
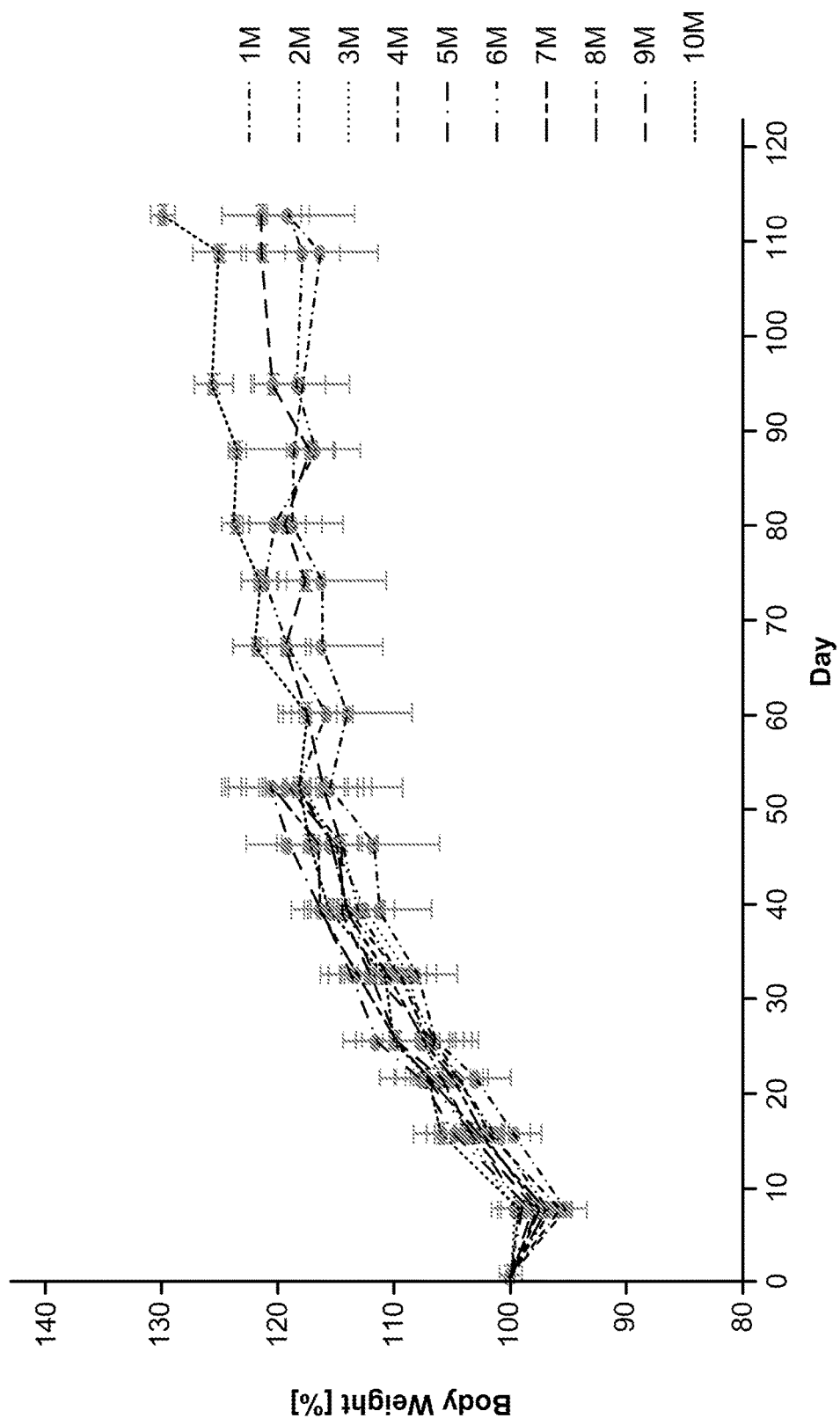
Figure 4:
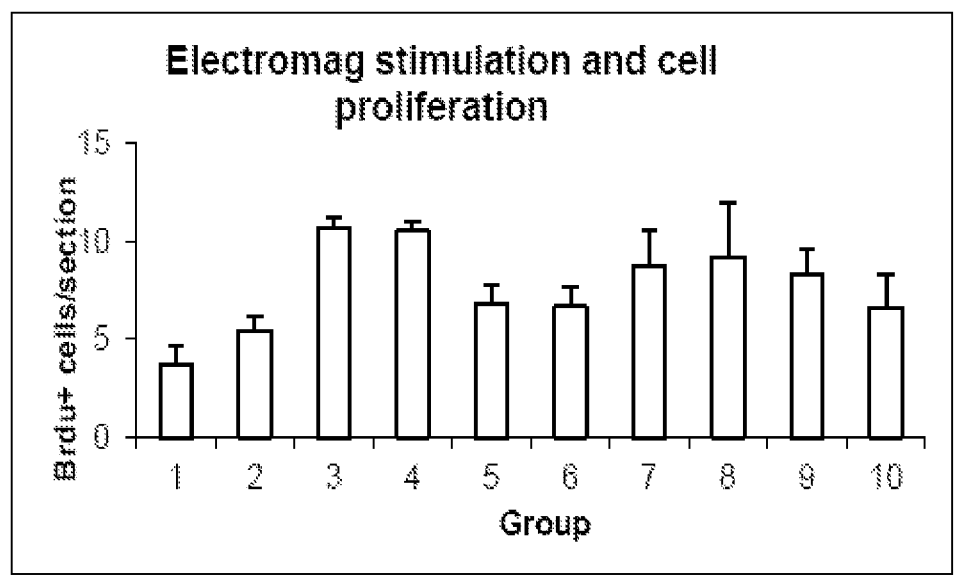
Figure 5:
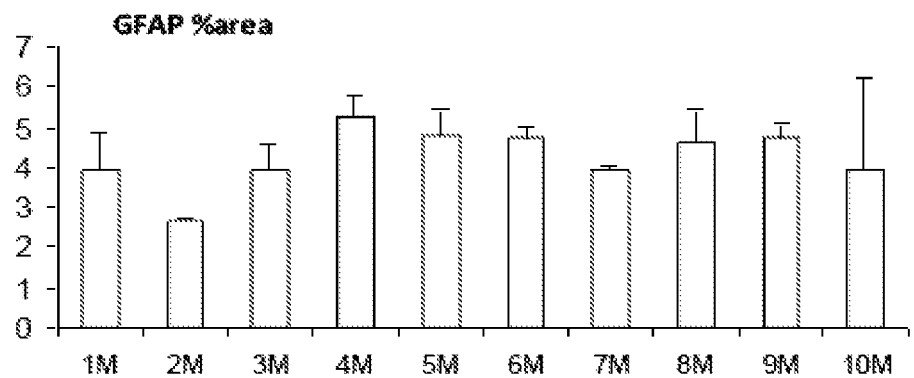
Figure 6:
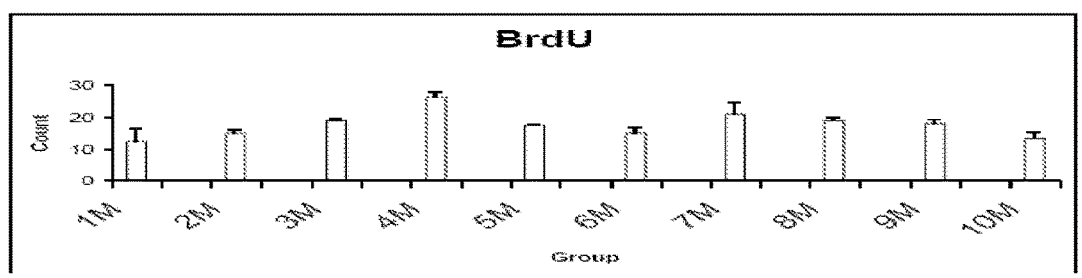
Figure 7:
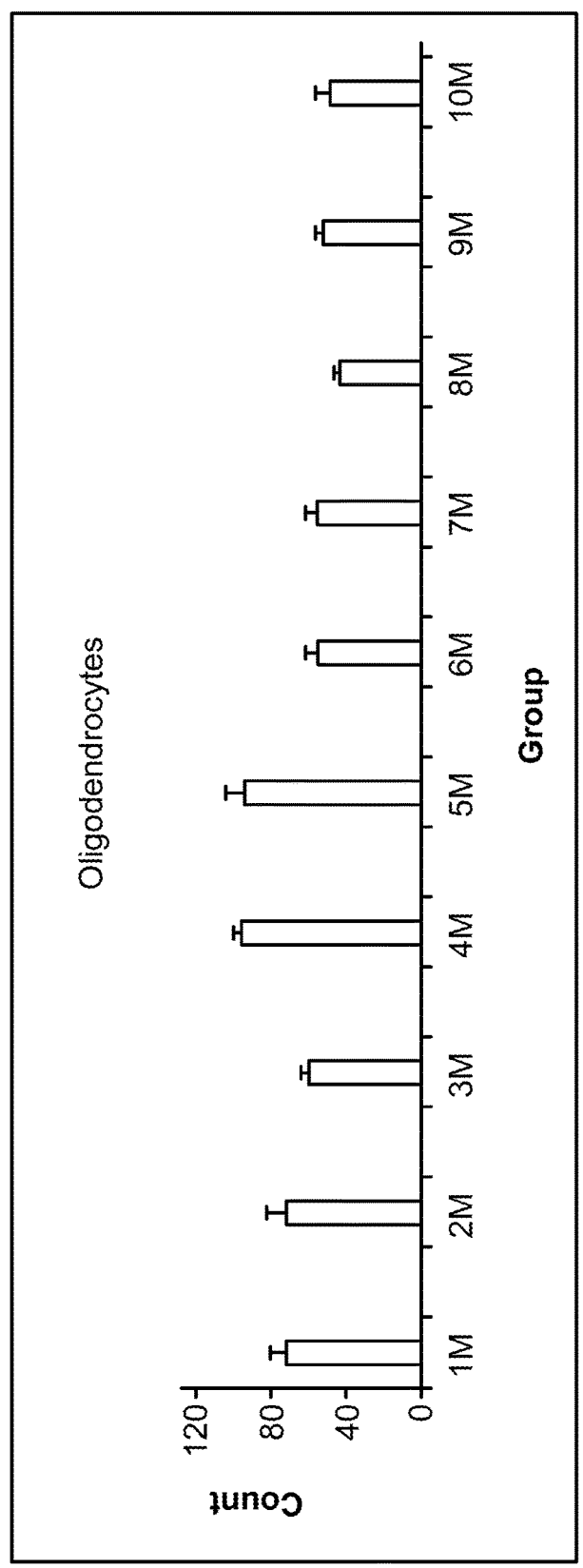
Figure 8:
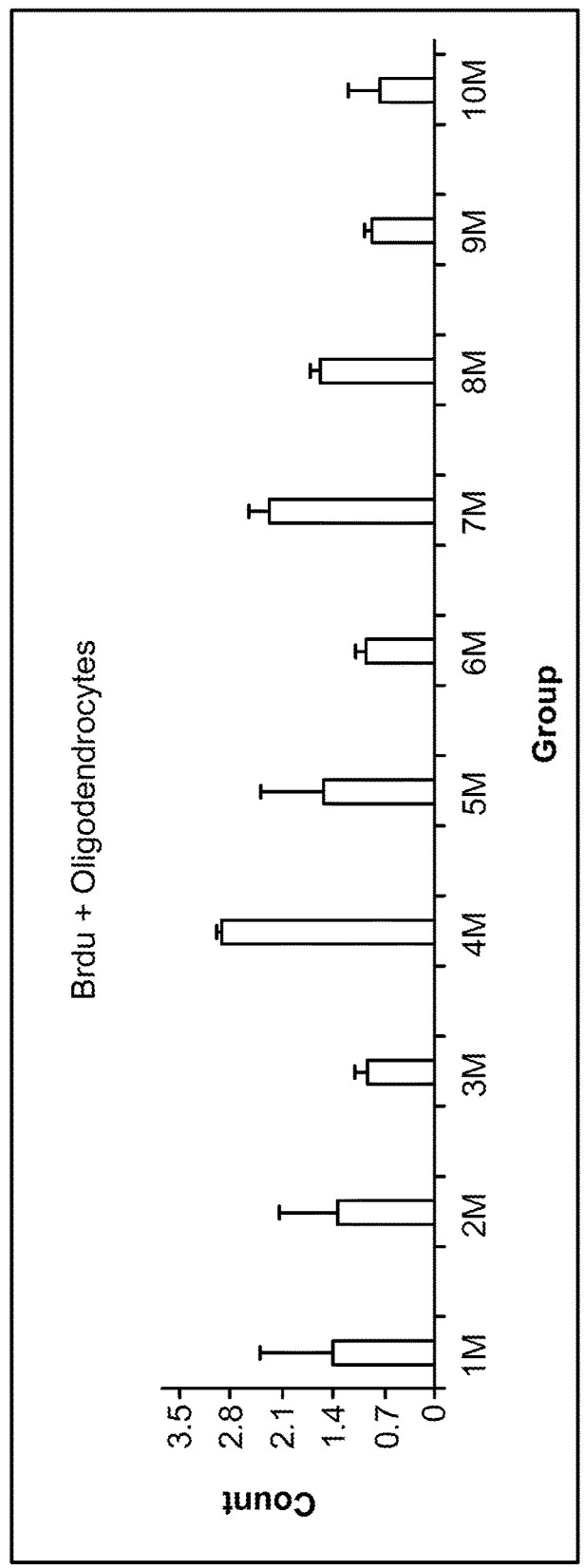
Figure 9:
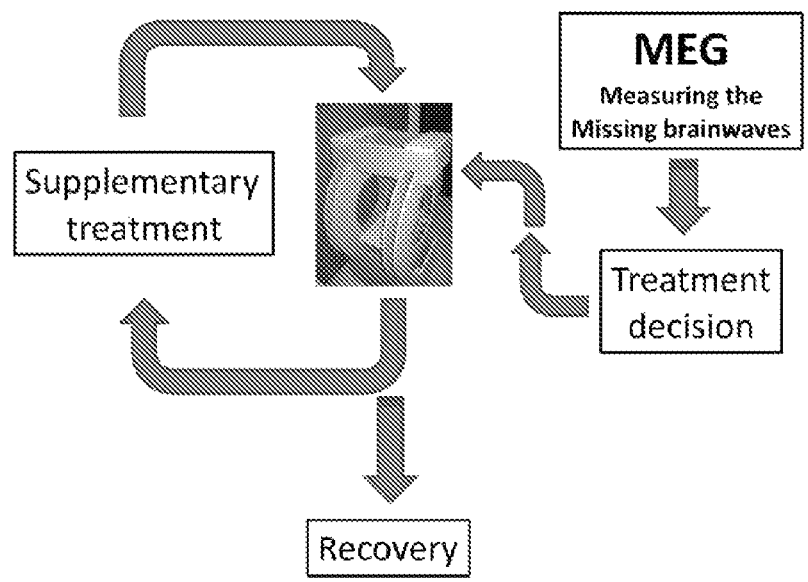
Figure 10:
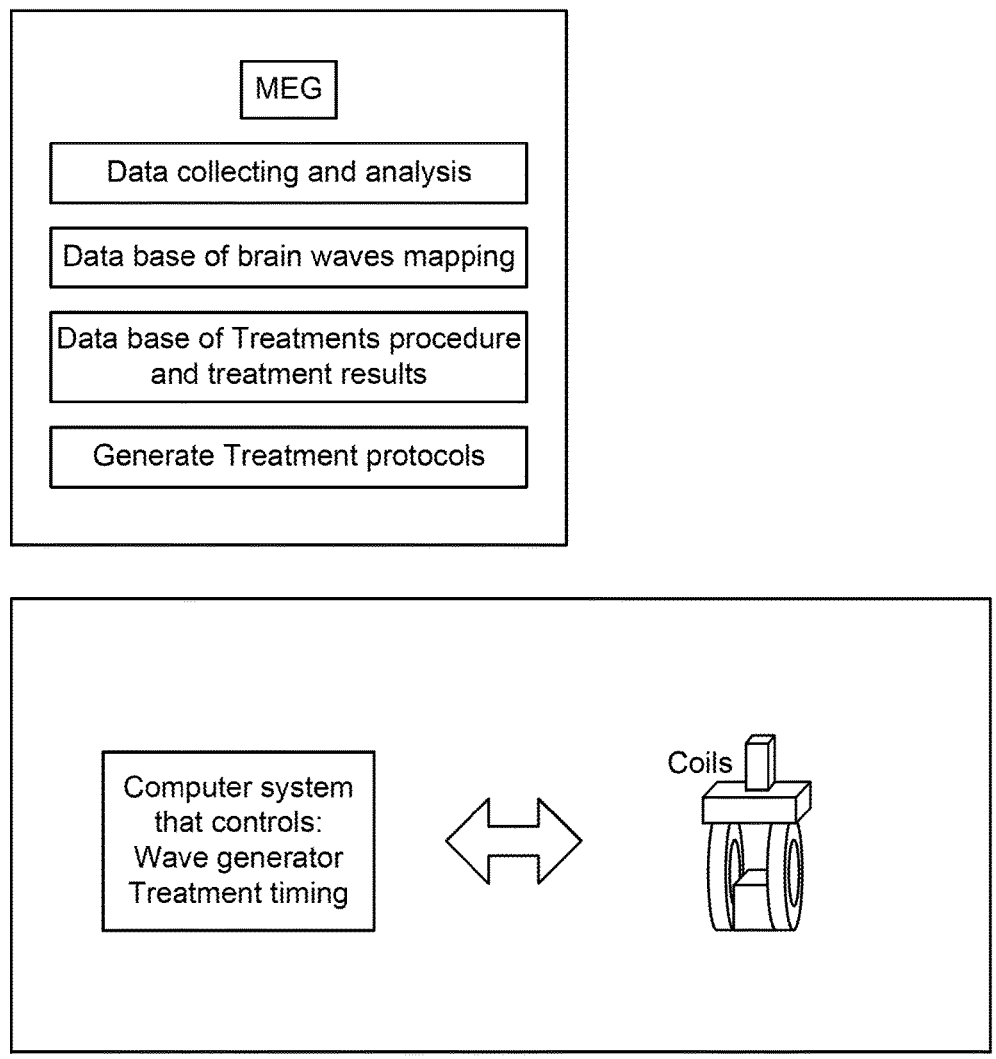
Figure 11:
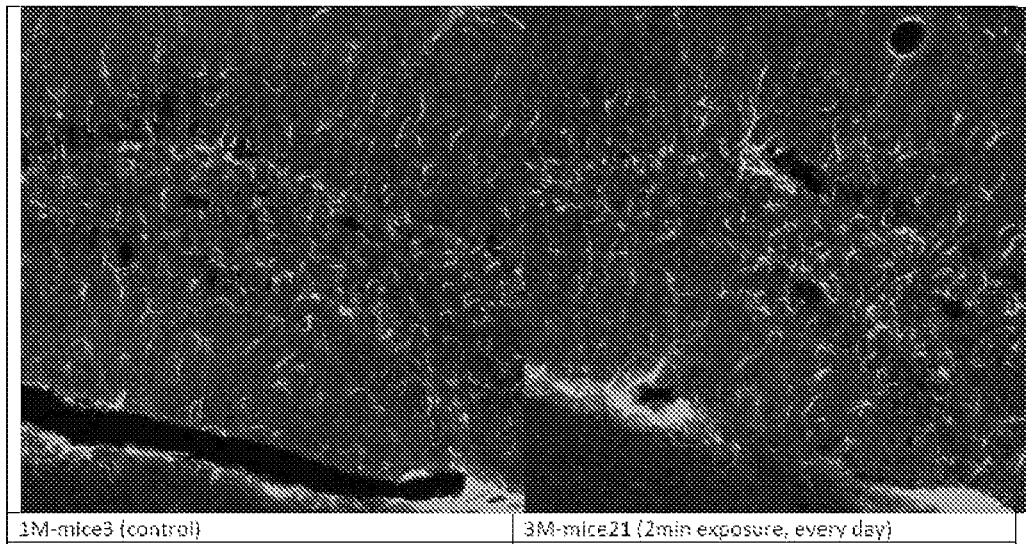
Figure 12:
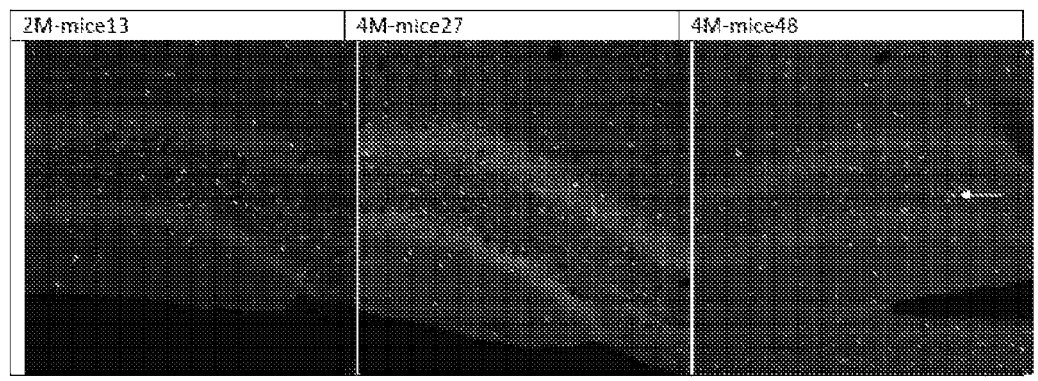
Figure 23:
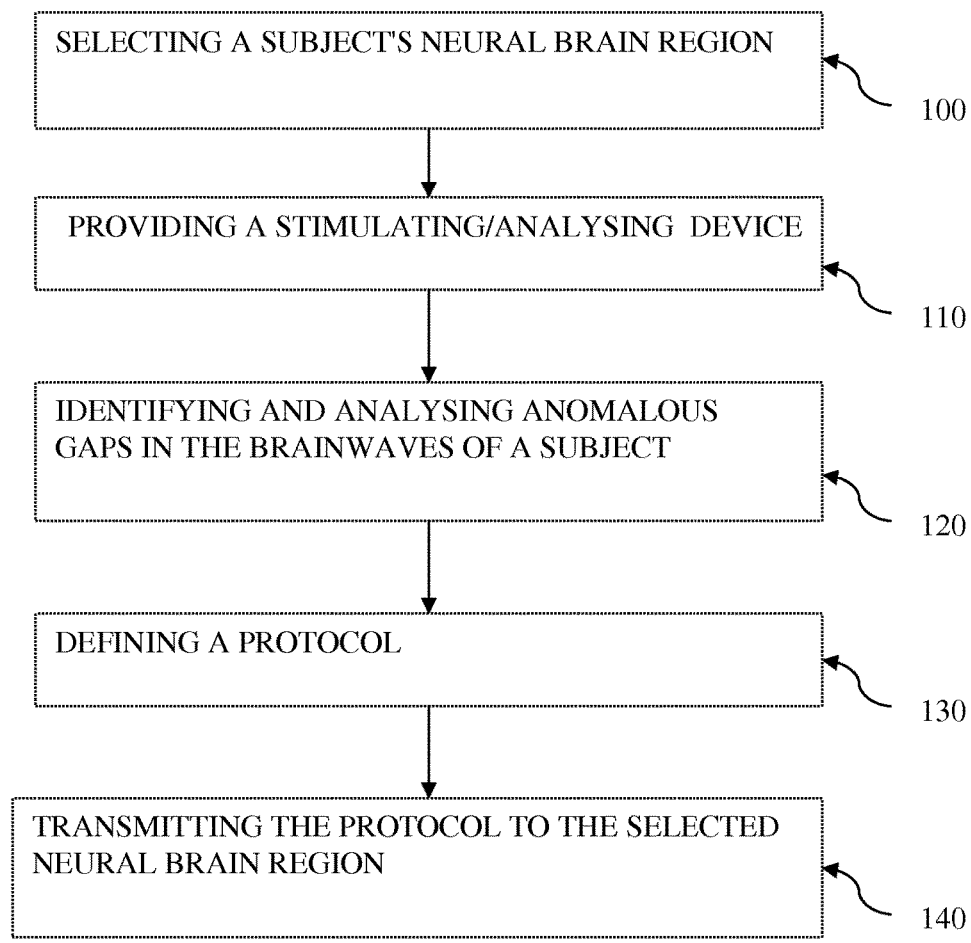

In order to understand the invention and to see how it may be implemented in practice, a few preferred embodiments will now be described, by way of non-limiting example only, with reference to be accompanying drawings, in which:

FIG. 1a-b illustrates a simplified model of the brain regions exposed to the electromagnetic stimulation device, in accordance with a preferred embodiment of the present invention;

FIG. 2 presents a graph with the results of social interaction test, in accordance with a preferred embodiment of the present invention;

FIG. 3 presents a graph of normalized body weight, in accordance with a preferred embodiment of the present invention;

FIG. 4 presents a graph of electromagnetic stimulation with cell proliferation, in accordance with a preferred embodiment of the present invention;

FIG. 5 presents a graph of the GFAP percentage area, in accordance with a preferred embodiment of the present invention;

FIG. 6 presents a graph of the BRTU count, in accordance with a preferred embodiment of the present invention;

FIG. 7 presents a graph of Oligodendrocytes count, in accordance with a preferred embodiment of the present invention;

FIG. 8 presents a graph of BRTU and Oligodendrocytes count, in accordance with a preferred embodiment of the present invention;

FIG. 9 presents images after brain neural networks with BrdU treatment, in accordance with a preferred embodiment of the present invention;

FIG. 10 presents images after brain neural networks with BrdU treatment, in accordance with a preferred embodiment of the present invention;

FIG. 11 presents a block diagram of the treatment procedure, in accordance with a preferred embodiment of the present invention;

FIG. 12 presents a block diagram of the apparatus and procedure, in accordance with a preferred embodiment of the present invention;

FIG. 13-22 present graphs of the exploration of possible pathology in the model of mild electromagnetic stimulation;

FIG. 23 presents a schematic diagram of the method for stimulating the nervous system of a subject brain, in accordance with a preferred embodiment of the present invention.

DETAILED DESCRIPTION

The following description is provided so as to enable any person skilled in the art to make use of the invention and sets forth the best modes contemplated by the inventor of carrying out this invention. Various modifications, however, will remain apparent to those skilled in the art, since the generic principles of the present invention have been defined specifically to provide device and method for stimulating the brain or different nervous system of a subject by means of the resonance effect between the frequency of a magnetic field directed to the subject and the natural brain wave frequency of the brain or nervous systems.

It is herein acknowledged that the present invention, without wishing to be bounded by science, works in the following way: A brain system functional unit comprises axons, nuerons and synapses, and the transmission between them is for a particular function. In other words, the brain functional unit described herein makes up or operates as an ad hoc network of cells connected in a pathway to achieve a single goal. Because of the brain's plasticity, the pathways are not necessarily permanent, and when a pathway is disrupted, another may be substituted or partially replaced by cell migration to the area of deficit.

The mode of action of the invention is by resonating the brain transmissions with a predetermined selected frequency according to a predetermined protocol. Without being bounded by theory, the present invention works on the principle that in addition to characteristic frequencies of electrical impulses traveling in the brain and through neural networks, and chemical pulses across synapses at predetermined wave frequencies, the present invention, for the first time, provides means of resonating the informational signals and frequencies at which these informational brain waves are propagated. An easy way to understand this is by considering the example of a subject who has had a stroke, and has subsequently been noted to have lost his sense of smell. When EM waves of the correct frequency are transmitted to the brain, the olfactory region of the brain will resonate as well as its surrounding regions, and cells from the surrounding regions will migrate to the olfactory region of the brain, thus at least partially repairing the deficit.

The effect obtained is that the increase activity in the specified nervous system will induce new brain cell regeneration, these newly generated brain cells are induced and recruited to migrate towards an area of the brain neural networks having the pathology or lesion of interest, thus initiating new brain cells that will be engaged in the existing pathways at the brain region of interest. The predetermined protocol is a treatment profile, comprising different frequency, transmission sessions and intensities. The protocol is adjusted to a brain system of interest of a specific subject.

The present invention further provides an electromagnetic stimulation apparatus and method which encourage the regeneration of new brain cells and stimulate them to migrate.

The term neural network herein used refers to a network or circuit of biological neurons.

The term further refers to artificial neural networks, which comprises artificial neurons or nodes. The neural network has distinct usages such as biological neural network.

Biological neural networks made up of real biological neurons that are connected or functionally related in a nervous system. In the field of neuroscience, they are often identified as groups of neurons that perform a specific physiological function in laboratory analysis.

A biological neural network is composed of a group or groups of chemically connected or functionally associated neurons. All neurons are electrically excitable, maintaining voltage gradients across their membranes by means of metabolically driven ion pumps, which combine with ion channels embedded in the membrane to generate intracellular-versus-extracellular concentration differences of ions such as sodium, potassium, chloride, and calcium. Changes in the cross-membrane voltage can alter the function of voltage-dependent ion channels. If the voltage changes by a large enough amount, an all-or-none electrochemical pulse called an action potential is generated, which travels rapidly along the cell's axon, and activates synaptic connections with other cells when it arrives. A single neuron may be connected to many other neurons and the total number of neurons and connections in a network may be extensive. The connections, known as synapses, are formed from axons to dendrites, though dendrodendritic microcircuits and other connections are possible. An axon, also known as a nerve fiber, is a long, slender projection of a nerve cell, or neuron, that typically conducts electrical impulses away from the neuron's cell body. Axons are in effect the primary transmission lines of the nervous system, and as bundles they help make up nerves. Axons make contact with other cells at junctions called synapses. Synapses are essential to neuronal function. Neurons are cells that are specialized to pass signals to individual target cells.

The key to neural function is the synaptic signaling process. At a synapse, the membrane of the axon closely adjoins the membrane of the target cell, and special molecular structures serve to transmit electrical or electrochemical signals across the gap. Some synaptic junctions appear partway along an axon as it extends called en passant ("in passing") synapses. Other synapses appear as terminals at the ends of axonal branches. A single axon can innervate multiple parts of the brain and generate thousands of synaptic terminals.

Apart from the electrical signaling, there are other forms of signaling that arise from neurotransmitter diffusion.

The cognitive modeling field involves the physical or mathematical modeling of the behavior of neural systems; ranging from the individual neural level (e.g. modeling the spike response curves of neurons to a stimulus), through the neural cluster level (e.g. modeling the release and effects of dopamine in the basal ganglia) to the complete organism (e.g. behavioral modeling of the organism's response to stimuli). Artificial intelligence, cognitive modeling, and neural networks are information processing paradigms inspired by the way biological neural systems process data.

The plasticity of the brain enhances brain operation capabilities upon increasing brain use of a specified system within the brain. In other words, brain region which has a deficit is identified.

FIGS. 1a-b present a simplified model of the brain regions which are exposed to electromagnetic waves transmitted by the device of the present invention. In reality, some nervous systems may stretch from one side of the brain to another, bypassing and/or overlapping other nervous systems or even co-existing in the same physical region. In FIG. 1a, the device transmits electromagnetic wave frequency to a region having an activity of interest "A", which includes and surrounds region "a" having operating frequency means, "$Haz_1$". Electromagnetic waves having a predetermined frequency "$Haz_1$" selected as appropriate for the particular deficit region, "recruit" cells from region "A", which respond to the same predetermined frequency as region b and induce migration of region "A" cells into region "a". Therefore other nervous regions such as "B", "C", "D", "E" having different operating frequencies such as "$Haz_2$" (frequency of region "B"), "$Haz_3$" (frequency of region "C"), "$Haz_4$" (frequency of region "D") will not resonate and therefore will not be active in response to the transmission.

The same is illustrated in FIG. 1b, the device transmits electromagnetic wave frequency to a region having an activity of interest "B", which includes and surrounds region "b" which having operating frequency means, "$Haz_2$". Electromagnetic waves having a predetermined frequency "$Haz_2$" selected as appropriate for the particular deficit region, "recruit" cells from region "B", which respond to the same predetermined frequency as region "b" and induce migration of region "B" cells into region "b". Therefore different nervous regions such as "A", "C", "D", "E" having different operating frequencies such as "$Haz_1$", "$Haz_3$", "$Haz_4$" will not resonate and therefore will not be active in response to the transmission.

The device of the present invention promotes the brain neural networks to regenerate and migrate new brain cells or their neurons to the determined nervous region. By generating an electromagnetic field having the same frequency as the determined nervous system, a resonance effect is created which generates electro-chemical transmission in the nerve cells and neuron of the determined nervous region, therefore promoting the process of regenerating brain cells.

The device of the present invention relays on the fact that each region or system in the brain has its own operating frequency means. This means that the transmission of electromagnetic waves do not have to be targeted to a specific region of the brain. Instead, the transmission of a particular frequency over the whole brain will exert an effect on the relevant nervous system alone. Therefore nervous system, having different operating frequencies will not resonate and therefore will not be active in response to the transmission.

The present invention further demonstrates that the nervous system frequency is one of the factors governing the activation of the nervous system.

The present invention further presents that different parts and function of the same nervous system which are activated by the transmission of different field intensities. The examples further demonstrates that both intensity and duration of the treatment has different outcomes, such that transmission is a 3D array when frequency, intensity and duration play a role in determining the exact nervous system and its desired section is targeted for enhancing its operational capabilities. Therefore, reducing the symptoms of the patient syndrome or condition.

The term "brain", "brain system", "brain neural network" or "nervous system" as used herein should be further understood also as including any nervous system or pathway within the brain and other peripheral systems.

The term "frequency" as used herein relates to a direct transmission in a given frequency or transmission of at least two frequencies which result in at least two waves having the given frequencies such as 100 Hz and 120 Hz, when combined generates two different frequencies of 10 Hz and 110 Hz.

The term "resonance" or "resonance effect" as used herein relates to the effect that occurs when a given electromagnetic field transmission, having the similar frequency of the natural operating frequency of a given nervous system, generates a neurotically activity in that system. Each nervous system can be described as a set of electro-chemical networks which has a specified operating frequency which allows it to transmit information from one nerve cell to other nerve cells of the same nervous system, and at the same time. Different operating frequencies separate the nervous systems operation allowing the brain to function in parallel without inter-nervous system interferences.

When the transmitter is turned on, it endues transmission within the specified nervous system having the same frequency and by that enhances its operation. Once the transmission ends, the nervous system regains its normal activity.

The present invention provides an apparatus for stimulating the brain nueral network systems of a subject comprising: (a) at least one transmitter configured to generate an electromagnetic field through the brain of a subject, (b) at least one brain wave measuring device for detecting subject brain wave frequency, (c) a first CPU for processing data concerned with detection of brain wave frequency of a subject comprising a database adapted for storing and analyzing the natural and affected brain scans resulting from the measuring device. The database is further used for evaluating the treatment protocol, (d) a second CPU for processing data concerned with transmission of wave frequency to a specific brain region having an activity of interest, and (e) at least one computer readable medium containing a predetermined protocol for transmission of the electromagnetic wave frequency profiles by the transmitter.

The computer readable medium is adapted to instruct the transmitter to provide a resonance effect thereby inducing newly generated brain cells to migrate toward a brain tissue area having the pathology or lesion of interest, and initiating new brain pathways at the brain region of interest.

The present invention is already enabled to the extent that the innovative technology can identify the brain waves frequencies which can be associated to a specific disorder of the nervous system, and the appropriate brain waves are utilized in the recovery treatment as determined according to the MEG (magnetoencephalography) data. This is performed by subjecting a patient to an ongoing series of electromagnetic exposures and supplementary treatment, and then targeting the nervous system which is with the need to be enhanced or treated. The rehabilitation process may be accompanied by para-medical treatment that will enhance the effect of the device and will relate to other aspects of recovery which are not necessary related directly to medical issues.

It is well known, according to Maguire E. A. et al (1997), that while the individual brain development is governed purely by genetics, the plasticity of the brain may play a significant role, even during the maturity of brain development. Such plasticity exemplifying process is manifested e.g. during the early stages of a recovery from a brain injury (e.g. accidental or stroke related) where a physical stimulation is conventionally carried out in order to increase brain activity in those brain regions affected by the trauma. In many cases, there is a recognizable increase in brain activity in such brain regions or in close regions which restore activities that have been lost during the traumatic event. There are, however, nervous systems in the brain that cannot be stimulated by a physiotherapy involving sensual activities such as vision, hear, smell or the like. Such nervous systems, once affected by trauma, will not be restored since there is no known way to artificially activate them and stimulate brain plasticity to increase their activity.

It is well known that while the brain is operating, it transmits electrical brain waves. Those waves allow the recognition, estimation and recordation of brain activity using instruments such as E.E.G. and M.E.G. The human brain waves range from the frequency of 0.01 Hz to about 100 Hz. In recent years it has been recognized that some brain systems operate in specific frequencies. For example, 10 Hz frequency is associated with the sympathetic nervous system that controls, among others, temporary changes in pupil size. Artificial stimulation using transcranial magnetic stimulation (TMS) in pulses that transmit direct energy to the targeted area in the brain assuming to generate natural pulses in the desired nervous system. In contrast to TMS systems, the present innovation is configured to encourage transmission within the brain neural networks by resonance effects in specified nervous system in the brain by transmitting electromagnetic of low frequency waves ranging from 0.01 Hz (DC) to about 100 Hz while the exact frequency will be correlated to a brain system of interest by a electromagnetic frequency profile which is discussed in detail in separate sections of the present disclosure. In addition, the presented results show that brain activity is not determined by frequency alone. The results presented show that treatment intensity (power and duration) has different effect on different parts of a given nervous system. Giving the thought that parts of the system are activated in different operating intensity, separating activity according to stimulation (natural or artificial). The range of intensity varies from 10 in the power of −6 Gauss to 100 Gauss, and treatment time from a few minutes to hours.

The apparatus comprising at least one measuring device for detecting the brain wave frequencies associated with the brain's nervous systems of interest.

The invention further relates to an apparatus comprising at least one transmitter configured to generates a substantially electromagnetic field, the transmitter comprises a positioning system configured to maintain the subject head in a predetermined position respective to at least one electrical coil. The coil provides a magnetic field through the subject head, wherein the coil is electrically connected or connectable to an alternating current supply unit. The current supply unit is under control of a treatment profile processing unit capable of determining the frequency, the level and the duration of the current supplied to the at least one coil according to a brain system of interest to be stimulated.

The stimulation apparatus of the present invention preliminary activates the nervous system for increasing the brain activity of the nervous system and for finally enlarging the number of the active brain cells in the desired brain paths.

The invention further relates to a method of transmitting different electromagnetic fields of specified frequencies in a homogeneous field covering the whole volume of the brain which resonates with the specified nervous system, The electromagnetic field frequencies varies from 0.01 Hz (DC) to 100 Hz, in intensities ranges from 10 in the power of −6 Gauss to 100 Gauss of transmitting duration ranges from minutes to hours.

The method further comprises the step of selecting a frequency within the range of frequencies for specific brain neural networks known to be capable of having the activity of interest.

The method is performed by exposing the subject brain to a magnetic field and alternating the selected frequency, thereby directing the magnetic field toward a brain tissue by means of resonance having the activity of interest.

By resonating the brain neural networks with the selected frequency, the enhanced activity promotes brain cell regeneration and newly generated brain cells are guided to migrate toward the brain tissue known to be capable of having the activity of interest, thereby initiating new brain paths at a brain nervous system or brain path of interest. The transmission of the magnetic field in the selected frequency may be repeated according to a predetermined protocol. Each session is for a predetermined duration during a time gap, within which the cell cycle of newly formed brain cells is initiated by synchronizing the transmission of the magnetic field with the cell cycle of the migrating newly generated brain cells for furthermore stimulating the creation of the new brain paths of interest. An additional aspect of the invention relates to a method for improving the capabilities of a human brain and/or to enhance brain activity, specifically of its nervous systems, the method comprises subjecting a brain to a transmission of electromagnetic waves in both frequency and intensity similar to these expected from natural brain waves normally originating in brain paths of interest, thereby selectively stimulating brain paths of interest and increasing their activity.

In a preferred embodiment of the invention the transmission is repeated according to a predetermined protocol, each time for a predetermined duration. The protocol is further adapted for additional transmitting for a short duration during a time gap which the cell cycle of newly formed brain cells is expected. The expectation may rely on experience, experimentally obtained data tables and/or response curves, calculations, imaging of the specific brain, undergoing the protocol to respond to a previous short duration transmission by the initiation of a new cell division cycle, thereby synchronizing the transmission with the cell cycle and guiding newly formed brain cells to migrate into regions where the improved capabilities are desired.

For instance: a more frequent, longer and intense exposure duration will be required in a case when the initial activity of a brain region is of a low intensity, in comparison in a case when the initial activity is of moderate intensity a less intensive treatment may be sufficient for generating a desired response.

The apparatus and method are not limited to specific brain paths. The apparatus enhances the brain activity of interest by encouraging brain cell formation in brain paths of interest.

The attribution of the brain waves to a specific region is identified when they are in subnormal intensity. Compensatory brain waves are generated artificially and directed to regions which are suspected of having a deficit in brain cells in their associated paths.

Transmitting the frequency and intensity of the specific electromagnetic waves encourages cell formation in at least one nervous system of deficit.

Another embodiment of the present invention further discloses an apparatus comprising:

a brain wave measuring device, and a brain waves transmission device.

The measuring device measures the brain frequencies and further determines the brain region of those specific frequencies (preferably a MEG system). The measuring device further adapted for mapping the brain neural networks and transmitting the frequency needed to invoke the "healing" treatment process. The present invention may further includes physio-therapy, psychologists or other therapies to enhance the effect of the device and accelerate the "healing" process.

The brain waves measuring device is monitored by means of EEG, MEG or by any other acceptable monitoring means. The brain waves measuring device and the brain waves transmission device are associated to brain nervous systems and/or functions.

Furthermore, the two devices may be integrated into one measuring unit comprising two units: a measuring unit and a transmission unit. The measuring unit comprises a sensing system (EEG/MEG/MRI) configured to define the characteristics of brain waves which are related to the brain system aimed to be stimulated. The sensing system further comprises complex analysis software or imaging algorithms configured to generate a correlation between the brain systems and respective brain waves frequencies. When a brain wave of interest is detected, transmission sessions can be started. The same measuring system may be used for evaluating the results of the transmission sessions. For instance, a person intended to undergo the procedure will be exposed to specific stimulation which is associated with a specific brain function of interest. The growth of the activity of the brain waves of a specific frequency in the stimulated brain portion will be then monitored. Once a specific brain wave frequency is detected as associated with the brain function of interest the transmission unit is used (in case the two units are implemented in separate respective devices)

The brain wave measuring device according the present invention comprises a brain wave monitor comprising a MEG system, in a communication with apparatus of the present invention. Having visualization capabilities such as functional MRI, the functional MRI is capable of detecting the brain activity in specific brain systems, but not their brain waves frequencies, therefore the use of both systems may be preferred due to the fact that each compensates the other faults.

According to the present invention, subjecting the brain to the electromagnetic oscillating field is carried out at frequencies similar or identical, to the frequencies detected in the measuring device and associated with the brain functions of interest.

The electromagnetic oscillating field is generated by a set of coils while at least one coil is configured to generate substantially low frequency and low intensity fields within the apparatus. The electromagnetic fields generated by the coil are resonated with the brain nervous system, for enhancing its activity.

According to a preferred embodiment of the invention, at least one coil, while two coils system might be applied by, such as a Helmholtz coil, having a turn diameter greater than the average sized human's skull. In order to generate a homogeneous electromagnetic field in the volume between the coils, The diameter of the coil is twice the distance between two similar portions thereof constituting a Helmholtz coil having a gap in between for receiving the head of a treated person. If for example, the gap between the coil portions is 25 cm (10"), the diameter of the coil turns will be 50 cm (20").

The coil is dressed upon the subject head, between two substantially similar portions thereof for transmitting an electromagnetic field. The electromagnetic field stimulates the desired brain area by means of resonance effect between the magnetic field frequency and the natural brain wave frequency of the respective brain system.

The number of coil turns is a matter of design. The coil turns depend on the current to be used for generating the magnetic field and/or on the thickness and resistance of the wire from which the coil is prepared (for less current more turns will be required, and a smaller wire gauge will be used for maintaining a magnetic field of a predetermined intensity, and vice versa). Since the field inside the apparatus is uniform and the neurons in the brain do not have a preferred alignment, the subject's head can be placed inside without specifically locating it. Therefore the subject head may be oriented in any convenient alignment.

The present invention further comprises an alternating current supply unit configured to supply current to at least one coil, in a frequency, current level, and for time duration which can be determined by a human operator of the device according to predetermined treatment considerations.

Preferably, the apparatus of the present invention comprises a computerized processing unit or/and computer readable medium (e.g. a CPU), comprising a database with a treatment protocol which is selected from a plurality of predetermined treatment profiles stored in a memory unit either locally associated with the apparatus or available from a remote server.

The treatment profile is selected according to treated subject details, (such details include e.g. the patient's injury, location of injured brain tissue, and a missing and/or reduced function of brain waves frequency and/or activity signals).

The CPU unit may be instructed by its operator to automatically control the current supply for supplying currents to the at least one coils, according to the selected protocol. Since minor differences between the natural frequency of a brain system of interest may occur between different people, and in order to allow treatment of the CPU database, without preceding a specific analysis of a subject brain system, the computerized system may be configured to work in a sweep mode in which the frequency of the current is controlled during a treatment session. The database is further adapted for mapping predetermined brain function.

The apparatus and method are applied in order to increase brain activity, life expectancy and life quality for the following syndromes: Autism, Famillial dysautonomia, Brather Willy, Epilepsy, the spectrum of PDD, the spectrum of HDAD, retardation, CP, brain trauma, stroke, learning difficulties, brain related disabilities in general like depression, psychological illnesses and brain related syndromes. It is expected the decrease the symptoms of brain injuries (trauma), stroke, multiple sclerosis (MS). This treatment and apparatus thereof is contemplated to be implemented in order to decrease the symptoms of Alzheimer, dementia, Parkinson and other degradative diseases of the brain and nervous systems.

EXAMPLES

The method and apparatus were demonstrated on a group of mice. The mice were divided into ten groups set in pairs as demonstrated in Table 1 below:

| group | treatment | Exposure (min) | Termination day | #N |
|---|---|---|---|---|
| 1M | Control Daily | 0 | 54 | 6 |
| | | | 114 | 4 |
| 2M | Control every other day | 0 | 54 | 6 |
| | | | 114 | 4 |
| 3M | Control Daily | 2 | 54 | 6 |
| 4M | Control every other day | 2 | 54 | 6 |
| 5M | Control Daily | 4 | 54 | 6 |
| 6M | Control every other day | 4 | 54 | 6 |
| 7M | Control Daily | 6 | 54 | 6 |
| 8M | Control every other day | 6 | 54 | 6 |
| 9M | Control Daily | 8 | 54 | 6 |
| | | | 114 | 4 |
| 10M | Control every other day | 8 | 54 | 6 |
| | | | 114 | 4 |

Bromodeoxyuridine (5-bromo-2'-deoxyuridine, BrdU) was injected twice daily on days 1-5, and again on day 27 which is the last day of radiation treatment. The weight of the mice was examined throughout the whole period.

From day 27 to 53 the mice were left in their cages with no further treatment.

On day 53 the mice have undergo a social recognition test.

On day 54 the majority of mice were sacrificed for histological analysis while 16 mice were kept for 8 weeks and later (day 114) had a brain gross pathology examination. The figures below demonstrates that no abnormal growth in the mice brains was caused and the neuron analysis shows that neuron regeneration was increased by about 50% (from 50% of new cells in the control mice to 75% of new cells) in the groups 4 and 9 which stand to be the groups where the treatment have caused the most significant effect.

Example 1

FIG. 2 depicts the results of the social interaction test.

Cognitive function: In the last day of the second month, the mice were tested for social recognition, as a measure of their cognitive function. Mice were individually exposed to a juvenile mouse for 2 min and the time spent investigating it was recorded. 10 min later, the tested mouse was re-introduced to the juvenile and the time of re-investigation was measured. The same procedure was repeated 30 min later. The decrease in social interaction between the second time and the third time represents the recognition ability of the mouse to identify the juvenile mouse as "familiar", thus of lower interest.

The decrease in social interaction between the second time and the third time in respect to the initial encounter between them shows no differences between the groups.

FIG. 3 presents a graph of normalized body weight. Body weight was measured throughout the experiments and no differences between the groups were found, indicating that the mice did not suffer from any significant pain or stress during the exposure time.

In FIG. 4-5, though BrdU expression increased in stimulated groups, astrocyte proliferation, as reflected by immunore activity of GFAP (green color) was not increased by stimulation. Although group 4M shows a slightly larger GFAP area. As seen before, there is no correlation between the results and the exposure time (groups 1,3,5,7,9 or groups 2,4,6,8,10 respectively) although similar patterns can be observed (especially between the BRDU positive and GRAP area of groups 2,4,6,8,10). Pearson's R coefficient of correlation between BrdU and GFAP was 0.33 and not significantly different from zero.

FIG. 6-8 presents the increase in Oligodendrocytes in group 4M (and 5M) which can be contributed to later regeneration of cells (later to the last BRDU injection) this suggests that cell regeneration have occurred in a longer period of time than that limited between the BRDU injections.

FIG. 9 presents a block diagram of the treatment procedure. The MEG measures brain waves and where they come from, for identifying the missing brain waves and which nervous system will be addressed in the recovery treatment. The patient is subjected to an ongoing series of electromagnetic exposures and supplementary treatment targeting the nervous system which is specified to be enhanced.

FIG. 10 presents a Block diagram of the apparatus combined with the procedure. The apparatus comprises a measuring device such as MEG for detecting subject brain wave frequency, at least one transmitter comprising at least one coil, configured to generate an electromagnetic field through the brain neural networks of a subject, a first CPU for processing and analyzing data concerned with detection of brain wave frequency of a subject, a second CPU for processing data concerned with transmission of wave frequency to a specific brain tissue having an activity of interest; and at least one computer readable medium containing a predetermined protocol for transmission of the electromagnetic wave frequency profiles by the transmitter.

The database of the CPU which comprises the treatments procedure and the treatment results, controls the wave generator and the treatment timing.

FIG. 11 presents images of BrdU positive cells indicating of cell proliferation. Quantifying the number of BRDU positive cells (red color) shows that the mice subjected to 2 min radiation exposure (groups 3&4) show the largest number of Brdu positive cells (proliferating following treatment). The BrdU positive cells are also found to migrate away from their "niche", compared with the control mice.

FIG. 12 presents images of the electromagnetic stimulation effects on cell proliferation and oligodendrocytes in the hippocampal dentate gyrus (DG). BrdU (red) and olig2 (green) in mouse dentate gyrus. Oligodendrocytes "born" after BrdU treatment appear as orange-yellow (arrow in C). DAPI (blue) is a counterstain. The treatment parameters of group 4M produced the optimal increase in oligodendrocyte proliferation and survival (see quantification).

Example 2

Repeated exposure of young adult mice to mild electromagnetic stimulation is expected to bring about positive effects that emanate from neurogenesis. However, the very fact that an environmental stimulus can affect developmental processes in brain, calls for caution regarding possible negative effects on some brain structures that have been previously shown to be vulnerable to intervention with normal development. The present example presents an examination of these structures. The following further presents the rationale for focus on each structure.

Cortical thickness has been reported to be affected by a variety of treatments in the course of development (Duque 2012, Lee 2011, Wilson 2004, Zhou 2004). It is expected that a treatment with adverse effects would reduce cortical thickness, reflecting failure of development and/or loss of cells. In either case, subtle reduction in cortical thickness can be correlated with substantial deficits at the behavioral level.

The corpus callosum, which provides the bridge between the right and left cerebral hemispheres is sensitive to intervention with development (Abreu-Villaça 1999, Filgueiras 2005, Sun 1995). It is expected that a treatment with adverse effects would result in reduced thickness of the corpus callosum, reflecting failure of normal development. It is also expected that in such case there will be evidence of microglial activation, reacting to myelin pathology.

The cerebral ventricles, especially the lateral ones, are enlarged in several neurological disorders reflecting atrophy of per-ventricular brain structures (Abreu-Villaça 1999, Filgueiras 2005, Sun 1995). It is expected that if electromagnetic stimulation has subtle negative effects, they may be revealed in enlargement of the lateral ventricles. The dentate gyrus is where electromagnetic stimulation is expected to induce neurogenesis. In addition, the dentate gyrus is subject to many types of neuronal and hormonal stimulations. Stress, for example, was shown to induce subtle pathological changes in the dentate gyrus and adjacent hippocampal fields. If repeated electromagnetic stimulation induces subtle neuropathology, then it may be expected that the number of neurons would be reduced in dentate gyrus fields and that microglia would be activated.

FIG. 13-22 presents exploration of possible pathology in the model of mild electromagnetic stimulation.

Mice were sampled from groups 1M, 2M, 9M, and 10M. The specifics of the stimulation parameters for groups 9M and 10M were not known to the experimenter analyzing the histological data. Nevertheless, groups 1 and 2M represent controls and groups 9 and 10M represent long term repeated exposure to electromagnetic stimulation.

Brain tissue was prepared as described in the previous example. Coronal sections were cut on a cryostat and were 30 um thick and free floating.

Assessment of gross structure (cortical thickness, ventricular size) was performed in cresyl violet stained coronal sections. Using bright field microscopy and 2× objective, fields were sampled that contained the fronto-parietal cortex, corpus callosum, lateral ventricle and the hippocampus from two brain sections per mouse.

Assessment of microglia was performed in sections stained for microglia using rabbit anti iba-1 (from Wako, Japan) at a dilution of 1:4000, followed by donkey anti rabbit labeled with biotin, at a dilution of 1:400 and then with extravidin peroxidase, dilution of 1:200. The final color reaction was with diaminobenzidine. Using brightfield microscopy and 10× objective, fields were sampled from the dentate gyrus and corpus callosum.

Thickness of frontoparietal cortex, corpus callosum and cross sectional area of lateral ventricle was measured at anterior 0.4-0.7 mm from Bregma. Thickness of cortex was measured at the somatosensory region. Thickness of corpus callosum was measured at the midline. Number of cells and microglial activation in the dentate gyrus were measured at posterior 1.7-2.3 mm from Bregma. The number of cells per square millimeter is reported. Microglial activation was detected by differential thresholding to visualize the soma of microglial cells. The number of microglial cells per square millimeter is used to detect microglial proliferation and the optical density of microglial soma is used as an index of reactivity.

Figure 13:
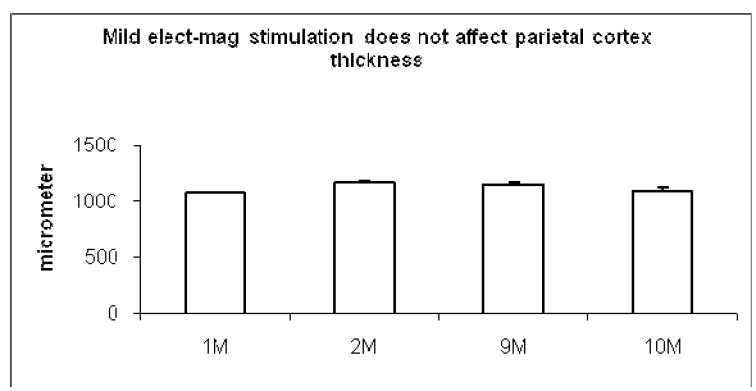
Figure 14:
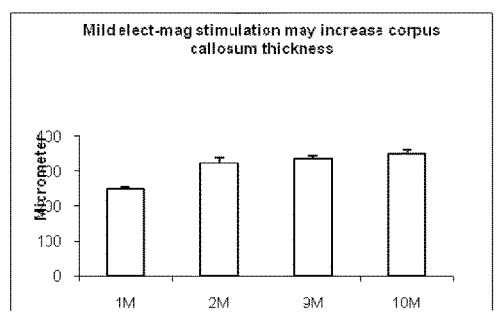
Figure 15:
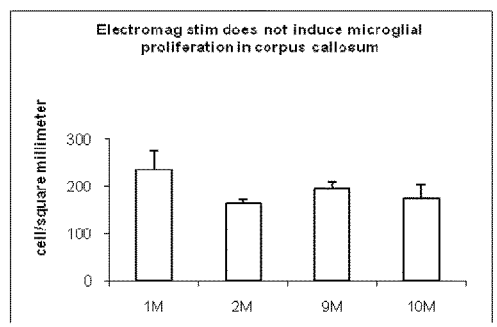
Figure 16:
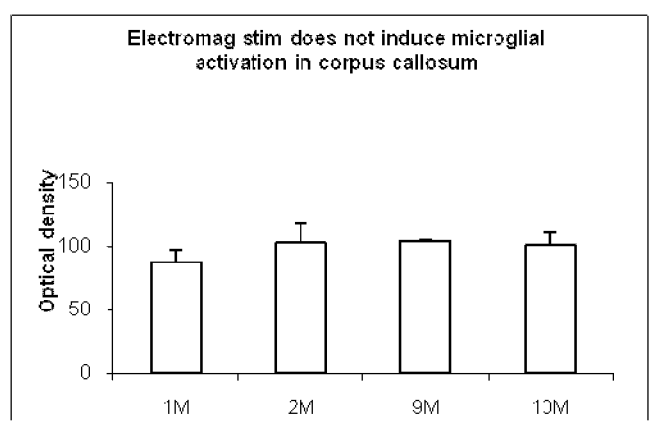
Figure 17:
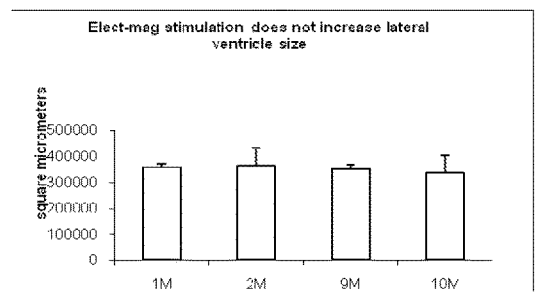
Figure 18:
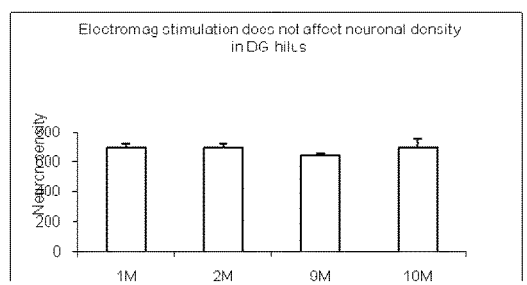
Figure 19:
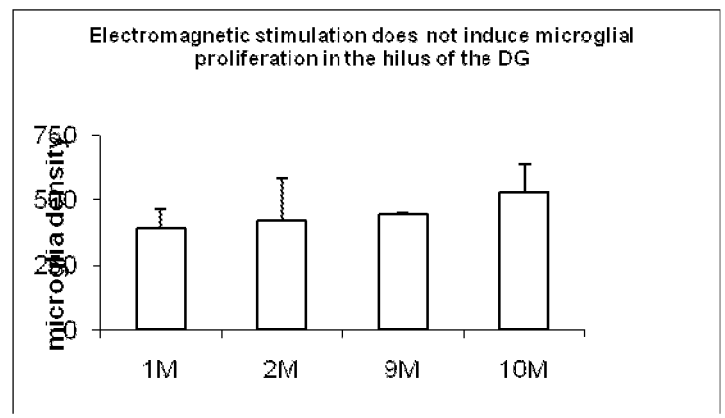
Figure 20:
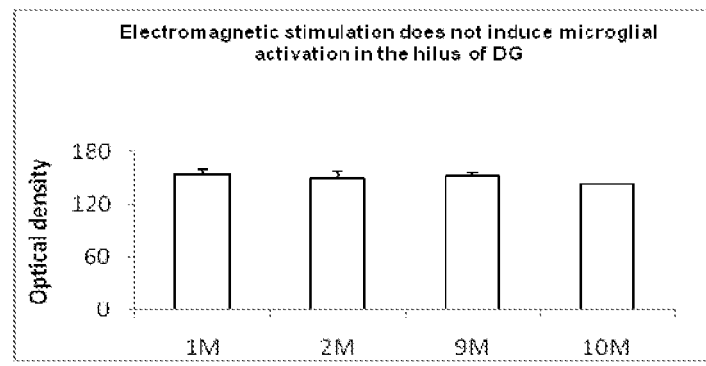
Figure 21:
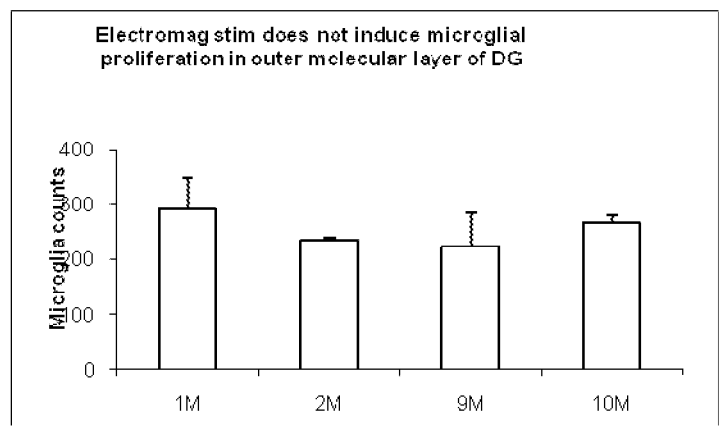
Figure 22:
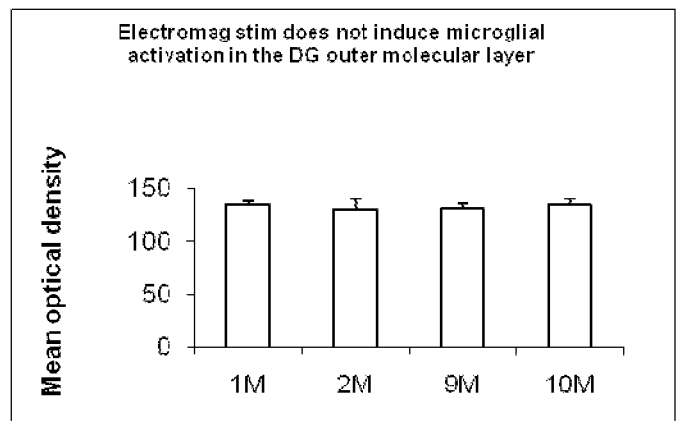

FIG. 13 presents a graph of Cortical thickness.
FIG. 14 presents a graph of Corpus callosum thickness:
FIG. 15 presents a graph of Corpus callosum—number of microglia.
FIG. 16 presents a graph of Corpus callosum—microglial activation.
FIG. 17 presents a graph of Lateral ventricle cross-sectional area.
FIG. 18 presents a graph of Dentate gyrus-density of neuron-size cells (cresyl violet stain).
FIG. 19 presents a graph of Dentate gyrus hilus (evidence for microglial proliferation)
FIG. 20 presents a graph of Dentate gyrus hilus (evidence for microglial activation)
FIG. 21 presents a graph of Dentate gyrus outer molecular layer (evidence for microglial proliferation)
FIG. 22 presents a graph of Dentate gyrus hilus (evidence for microglial activation) In the present example, no pathology was found in any of the brain structures that are known to be sensitive to intervention with developmental processes.

There may be a mild increase in the size of the corpus callosum. The number of animals in each group is too small for statistical determination. But this observation may hint to a trophic effect of mild electromagnetic stimulation on myelin formation.

FIG. 23 presents a schematic diagram of the method for stimulating the brain neural networks of a subject comprising the step of: (a) selecting a neural brain region of a subject, (b) providing an apparatus for stimulating a nervous system of a subject comprising:
  (i) at least one transmitter configured to generate an electromagnetic field through the nervous system of a subject; (ii) at least one brain waves measuring device for detecting subject brain wave frequency, (iii) a first CPU for processing data concerned with detection of brain wave frequency of a subject, (iv) a second CPU for processing data concerned with transmission of wave frequency to a specific brain tissue having an activity of interest; and (v) at least one computer readable medium containing a predetermined protocol for transmission of the electromagnetic wave frequency profiles by the transmitter;
  (b) identifying and analyzing anomalous gaps in the brainwaves of a subject;
  (c) defining a protocol, (d) transmitting to the subject nervous system the protocol on the selected neural brain region, wherein the step of defining the protocol includes providing an electromagnetic frequency profile including compensatory brainwaves; further wherein the protocol provides a resonance effect thereby inducing newly generated brain cells to migrate toward a brain tissue area having the pathology or lesion of interest, and initiating new brain pathways at the neural brain region.

There is further provided in accordance with a preferred embodiment of the present invention the method as defined above, further comprising the step of identifying a site of the pathological condition in the body of the subject, and wherein the step of selecting the body region comprises selecting a neural sensitive region of the body remote from the site.

There is further provided in accordance with a preferred embodiment of the present invention the method as defined above, wherein the step of transmitting the neural sensitive body region with at least one wave frequency comprises transmitting the neural sensitive body region with a plurality of frequencies, and comprising the additional step of maintaining a minimum chronological spacing between successive ones of the frequencies of several minutes.

There is further provided in accordance with a preferred embodiment of the present invention the method as defined above, further comprising a positioning system configured to maintain the subject head in a predetermined position respective to the transmitter.

There is further provided in accordance with a preferred embodiment of the present invention the method as defined above, wherein the electromagnetic field is adapted for stimulating the desired brain system by means of resonance effect between the frequency of the magnetic field and the natural brain wave frequency of the subject brain system.

There is further provided in accordance with a preferred embodiment of the present invention the method as defined above, wherein the CPU includes a database for mapping the brain wave of a subject in order to adjust to the subject the protocol.

There is further provided in accordance with a preferred embodiment of the present invention the method as defined above, wherein the CPU is further adapted to control the wave generator and the treatment timing.

There is further provided in accordance with a preferred embodiment of the present invention the method as defined above, wherein the protocol includes a plurality of distinct frequencies within the range of the distinct brain activities.

There is further provided in accordance with a preferred embodiment of the present invention the method as defined above, wherein the transmitter comprises a coil; the coil is a Helmholtz coil, having a turn diameter greater than an average sized human's skull.

There is further provided in accordance with a preferred embodiment of the present invention the method as defined above, wherein the frequencies are conformed in accordance to specific brain tissue known to be capable of having an activity of interest.

There is further provided in accordance with a preferred embodiment of the present invention the method as defined above, wherein the magnetic field is transmitted in a selected frequency for at least one session.

There is further provided in accordance with a preferred embodiment of the present invention the method as defined above, wherein the transmission of the magnetic field is synchronized with the cell cycle for migrating newly generated brain cells.

There is further provided in accordance with a preferred embodiment of the present invention the method as defined above, further wherein the stimulating procedure results the creation of the new brain paths of interest.

There is further provided in accordance with a preferred embodiment of the present invention the method as defined above, further wherein the transmitter operates within the frequency range of about 0.01 Hz (DC)-100 Hz.

There is further provided in accordance with a preferred embodiment of the present invention the method as defined above, wherein the electromagnetic field is administered in a range between about 10 in the power of −6 Gauss to 100 gauss that are found to resonant the nervous system in the brain.

There is further provided in accordance with a preferred embodiment of the present invention the method as defined above, is applied to certain diseases and syndromes such as Autism, Famillial dysautonomia, Brather Willy, Epilepsy, the spectrum of PDD, the spectrum of HDAD, retardation, CP Autism, Famillial dysautonomia, Brather Willy, Epilepsy, the spectrum of PDD, the spectrum of HDAD, retardation, CP, brain trauma, stroke, learning difficulties, brain related disabilities in general like depression, other psychological illnesses and other brain related syndromes or diseases.

There is further provided in accordance with a preferred embodiment of the present invention the method as defined above, further wherein the apparatus decrease the symptoms of brain injuries (trauma), stroke, multiple sclerosis (MS), symptoms of Alzheimer, dementia, Parkinson and any other degradation diseases of the brain. There is further provided in accordance with a preferred embodiment of the present invention the method as defined above, wherein the treatment protocol is adapted for determining frequency, level and duration of the current supplied to the transmitter according to a subject brain system, specified to be stimulated.

There is further provided in accordance with a preferred embodiment of the present invention the method as defined above, wherein the brain waves measuring device is selected from a group consisting of: EEG,MEG or by any other acceptable monitoring means.

There is further provided in accordance with a preferred embodiment of the present invention the method as defined above, wherein the brain waves measuring device comprises a combination of a sensing system such as EEG, MEG or MRI for defining the characteristics of brain waves of the predetermined brain system specified to be stimulated.

There is further provided in accordance with a preferred embodiment of the present invention the method as defined above, further wherein the measuring system is used for evaluating the results of the transmission sessions.

There is further provided in accordance with a preferred embodiment of the present invention the method as defined above, wherein the apparatus is applied to certain diseases and syndromes such as Autism, Famillial dysautonomia, Brather Willy, Epilepsy, the spectrum of PDD, the spectrum of HDAD, retardation, CP and other brain related syndromes.

There is further provided in accordance with a preferred embodiment of the present invention the method as defined above, further wherein the apparatus decrease the symptoms of brain injuries (trauma), stroke, multiple sclerosis (MS), symptoms of Alzheimer, dementia, Parkinson and any other degradation diseases of the brain. In the foregoing description, embodiments of the invention, including preferred embodiments, have been presented for the purpose of illustration and description. They are not intended to be exhaustive or to limit the invention to the precise form disclosed. Obvious modifications or variations are possible in light of the above teachings. The embodiments were chosen and described to provide the best illustration of the principals of the invention and its practical application, and to enable one of ordinary skill in the art to utilize the invention in various embodiments and with various modifications as are suited to the particular use contemplated. All such modifications and variations are within the scope of the invention as determined by the appended claims when interpreted in accordance with the breadth they are fairly, legally, and equitably entitled.

The invention claimed is:

1. An apparatus for stimulating a neural network of a brain of a subject, the apparatus comprising:
   a brain wave measuring device configured to determine a brain wave frequency of a region of the brain that is related to the neural network and that has a subnormal intensity;

at least one transmitter for generating a homogeneous electromagnetic field configured to cover a whole volume of the brain of the subject; and a unit for controlling said at least one transmitter according to a predetermined protocol to generate the electromagnetic field such that the field frequency is equal to the determined brain wave frequency, the electromagnetic field having an intensity and duration configured to induce a resonance effect between the electromagnetic field and the neural network.

2. The apparatus of claim 1, wherein the protocol is a treatment profile selected from a plurality of predetermined treatment profiles.

3. The apparatus of claim 2, wherein the treatment profile is stored locally.

4. The apparatus of claim 2, wherein the treatment profile is stored on a remote server.

5. The apparatus of claim 2, wherein the plurality of predetermined treatment profiles is stored in a memory unit.

6. The apparatus of claim 1, wherein the frequency is within a frequency range of about 0.01 Hz to 100 Hz.

7. The apparatus of claim 1, wherein the intensity ranges between 10 in the power of −6 Gauss to 100 Gauss.

8. A method for stimulating a neural network of a brain of a subject, the method comprising:

operating a brain wave measuring device to determine a brain wave frequency of a region of the brain that is related to the neural network and that has a subnormal intensity; and controlling, by a control unit, at least one transmitter to generate a homogeneous electromagnetic field configured to cover a whole volume of the brain of the subject, the electromagnetic field having a frequency that is equal to the determined brain wave frequency and having an intensity and duration configured to induce a resonance effect between the electromagnetic field and the neural network.

9. The method of claim 8, wherein the protocol is a treatment profile selected from a plurality of predetermined treatment profiles.

10. The method of claim 9, further comprising storing the treatment profile locally.

11. The method of claim 9, further comprising storing the treatment profile on a remote server.

12. The method of claim 9, further comprising storing the plurality of predetermined treatment profiles in a memory unit.

13. The method of claim 8, wherein the frequency is within a frequency range of about 0.01 Hz to 100 Hz.

14. The method of claim 8, wherein the intensity ranges between 10 in the power of −6 Gauss to 100 Gauss.

15. The method of claim 8, further comprising synchronizing the generation of the electromagnetic field with a cell cycle for migrating newly generated brain cells.

* * * * *